(12) United States Patent
Lindstrom et al.

(10) Patent No.: US 7,316,667 B2
(45) Date of Patent: Jan. 8, 2008

(54) LEAD INSERTION TOOL FOR HEMOSTATIC INTRODUCER SYSTEM

(75) Inventors: Curtis C. Lindstrom, Roseville, MN (US); James D. Kadera, Burnsville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 709 days.

(21) Appl. No.: 10/379,944

(22) Filed: Mar. 6, 2003

(65) Prior Publication Data

US 2004/0176781 A1    Sep. 9, 2004

(51) Int. Cl.
*A61M 5/178* (2006.01)
(52) U.S. Cl. .............................. 604/167.06; 604/164.05
(58) Field of Classification Search ................ 606/190, 606/192, 198, 185, 151; 604/167, 164, 169, 604/264, 164.01, 164.03, 164.04, 164.05, 604/164.07, 167.01, 167.03, 167.04, 167.05, 604/167.06; 600/201, 203, 204
See application file for complete search history.

(56) References Cited

U.S. PATENT DOCUMENTS

| 5,607,443 A | * | 3/1997 | Kieturakis et al. | .......... 606/192 |
| 5,779,697 A | * | 7/1998 | Glowa et al. | ............... 606/185 |

* cited by examiner

*Primary Examiner*—Kevin T. Truong
(74) *Attorney, Agent, or Firm*—Faegre & Benson LLP

(57) ABSTRACT

A tool for protecting a cardiac stimulating lead from damage upon passing through a hemostasis valve of a vascular introducer in the course of an implantation procedure comprises a splittable, peal-away sheath that is rendered sufficiently rigid by a tool dilator or placement of the lead body within the sheath so that the combination can be forced through a self-closing aperture formed through the hemostatic valve member. The use of the tubular sheath in breaching the self-closing aperture shields the lead electrodes and any covering that may be present from becoming distorted as well as from contamination by silicon oil commonly found in vascular introducers having a hemostasis valve.

12 Claims, 3 Drawing Sheets

LEAD INSERTION TOOL FOR HEMOSTATIC INTRODUCER SYSTEM

BACKGROUND OF THE INVENTION

I. Field of the Invention

This invention relates generally to implantable tissue stimulating apparatus of the type having a pulse generator and a medical lead for delivering electrical stimulation to target tissue, and more particularly to a tool to be used in facilitating the surgical implantation of a medical lead into a patient's body.

II. Discussion of the Prior Art

In implanting medical devices, such as pacemakers or pacemakers/defibrillators, a transvenous lead placement approach has found wide acceptance. Using the Seldinger technique, the right or left cephalic vein or the axillary vein is located and punctured with a relatively long, large-bore needle. A guidewire is then typically passed through the needle into the selected vein. The needle is then removed from the guidewire and replaced with an introducer incorporating a hemostasis valve to stem blood flow. Once the introducer is in place, the medical lead is forced through the hemostasis valve, the introducer's shaft, and thence, through the selected vein and ultimately into a selected chamber of the heart.

An introducer that has found rather wide spread acceptance is the SafeSheath® manufactured and sold by Pressure Products of Rancho Palo Verdes, Calif. It incorporates a tear-away sheath having a break-away hemostasis valve assembly affixed to a proximal end of the sheath. The hemostasis valve assembly comprises a molded plastic housing containing an elastomeric disk having a self-closing aperture formed through its thickness dimension. The SafeSheath also includes a side entry port located distally of the housing containing the hemostasis valve whereby fluids containing an anti-coagulant may be infused through the lumen of the sheath and into the selected vein.

Once the introducer is installed, a medical lead having one or more electrode surfaces at its distal end is passed through the hemostasis valve of the introducer and thence, through its sheath until the electrodes are positioned at a desired site within the heart. Once the distal end of the lead is appropriately placed, the introducer may be removed from the lead by splitting the break-away hemostasis valve assembly and the sheath.

While introducers of the type described can be used with a variety of pacemaker/defibrillator leads, there are certain lead designs that can be damaged as the distal end portion bearing the electrodes is forced through the self-closing aperture of the hemostatic valve. The shocking electrodes on defibrillator leads are often in the form of an uninsulated wire coil supported by the lead's plastic body. As a lead of this type is forced through the hemostasis valve of an introducer, the excessive frictional forces tend to displace the turns of the coil so that they are no longer appropriately spaced.

Other leads with which the SafeSheath introducer is incompatible are those in which a fabric covering is placed over the coil electrodes of defibrillator leads to inhibit tissue ingrowth into the coils of the shocking electrode. Because of the porosity of the fabric, electrical shocking currents readily pass through to surrounding tissue with very low impedance. However, it is found that the SafeSheath introducer incorporates a silicon oil as a lubricant on its hemostasis valve member and as such a fabric covered electrode of the lead is forced through the self-closing aperture, the silicon oil wipes off onto the fabric covering that tends to plug the pores in the fabric which adversely impacts the lead's electrical performance. Then, too, when attempting to pass this lead through the valve, frictional forces tend to displace the fabric covering, in effect, peeling it back. Another drawback of the hemostatic valve's direct engagement with the medical lead being implanted is that tactile feedback through the lead to the physician's fingers is severely dampened.

From the foregoing discussion, those skilled in the art will appreciate that a need exists for a lead insertion tool that will obviate the cited drawbacks of state-of-the-art lead introducers incorporating a hemostasis valve. The present invention provides such a device.

SUMMARY OF THE INVENTION

The present invention comprises a lead insertion tool adapted for use with a lead introducer having an elastomeric hemostasis valve with a self-closing aperture. The tool comprises a tubular sheath having a relatively thin wall with at least one longitudinal groove formed inwardly thereof to facilitate rupture of the sheath along the groove. The lumen of the tubular sheath is sized to receive a medical lead therethrough with a predetermined clearance fit. A tool dilator that has a generally rigid shaft is insertable through the lumen of the tubular sheath and when so inserted renders the sheath sufficiently rigid to allow insertion of the sheath and dilator through the self-closing aperture of the lead introducer. Once inserted through the aperture, the tool dilator is removed from the tubular sheath and the distal end of the medical lead is then advanced through the lumen of the sheath which holds the aperture in the hemostasis valve open while shielding the lead from exposure to contaminating silicon oil and minimizing friction that distorts the lead electrodes and/or fabric covering. Once the lead has made its way past the hemostasis valve, provision is made for rupturing the tubular sheath of the insertion tool along its length, allowing it to be pealed off from the lead body.

In accordance with a further feature of the invention, the tool dilator may be dispensed with when the lead insertion tool is assembled onto the distal end portion of the lead to be installed and then the lead with the tubular sheath surrounding its distal end are passed through the hemostasis valve as a unit.

DESCRIPTION OF THE DRAWINGS

The foregoing features and objects, as well as others, will become apparent to those skilled in the art from the following detailed description of a preferred embodiment, especially when considered in conjunction with the accompanying drawings in which.

DESCRIPTION OF THE PREFERRED EMBODIMENT

Figure 1:
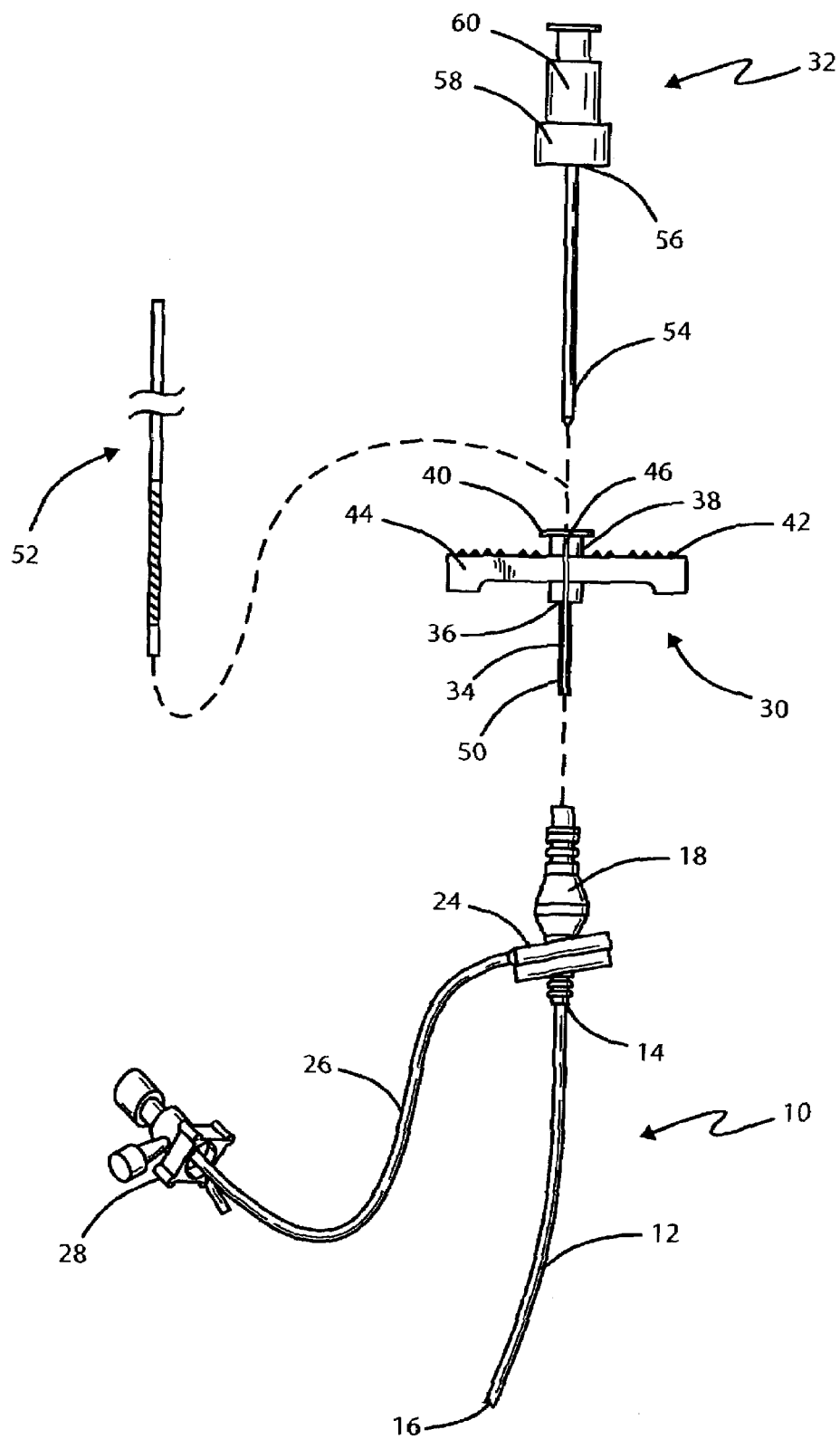
FIG. 1 is an exploded side elevational view of the lead insertion tool comprising a preferred embodiment of the present invention.

Certain terminology will be used in the following description for convenience in reference only and will not be limiting. The words "upwardly", "downwardly", "rightwardly" and "leftwardly" will refer to directions in the drawings to which reference is made. The words "inwardly" and "outwardly" will refer to directions toward and away from, respectively, the geometric center of the device and associated parts thereof. Said terminology will include the words above specifically mentioned, derivatives thereof and words of similar import.

Figure 2:
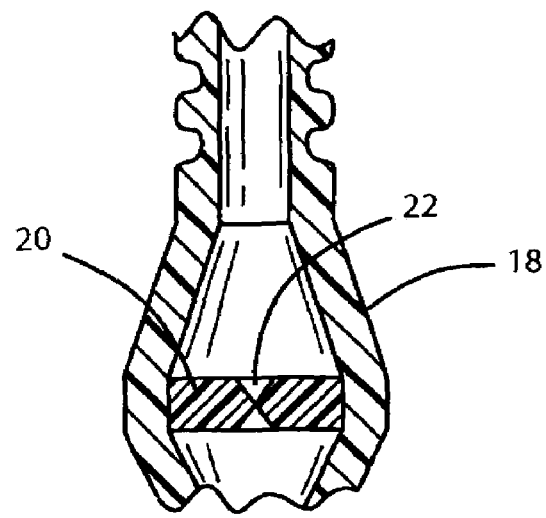
FIG. 2 is an enlarged view of the hub portion of a lead introducer showing the hemostasis valve.

Referring initially to FIG. 1, there is indicated generally by numeral 10 a conventional introducer set of a type used in implanting medical leads for an implantable pacemaker or pacemaker defibrillator. It is seen to comprise a flexible, tubular sheath 12 having a proximal end 14 and a distal end 16 and with a lumen extending therebetween. Completing the set is a dilator (not shown). Affixed to the proximal end 14 of the sheath 12 is a hub member 18 that is molded from a suitable plastic. Contained within the hub 18 is an elastomeric disk 20 (FIG. 2) having a self-closing aperture 22 formed through the thickness dimension thereof. The hub 18 further includes a side port 24 having a bore, not shown, that is in fluid communication with the lumen of the sheath 12. A length of tubing 26 may be connected to the side port 24 and affixed to the other end of the tubing 26 is a stop cock member 28. This stop cock is also a conventional component and has provision for controlling the flow of a flushing fluid, such as saline or saline mixed with an anti-coagulant to inhibit plugging or clogging of the sheath 12 by blood.

For illustrative purposes only, the introducer set 10 may comprise a SafeSheath introducer of Pressure Products, Inc. or another introducer set incorporating a hemostatic valve.

Figure 3:
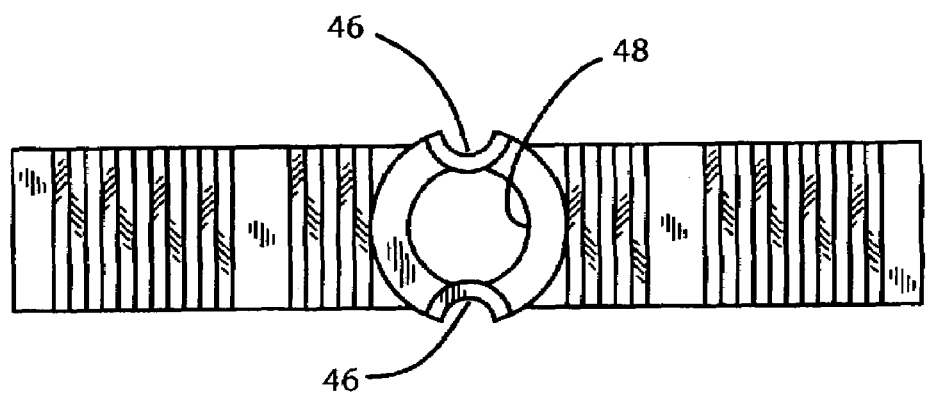
FIG. 3 is a top plan view of the tubular sheath component shown in FIG. 1.
Figure 4:
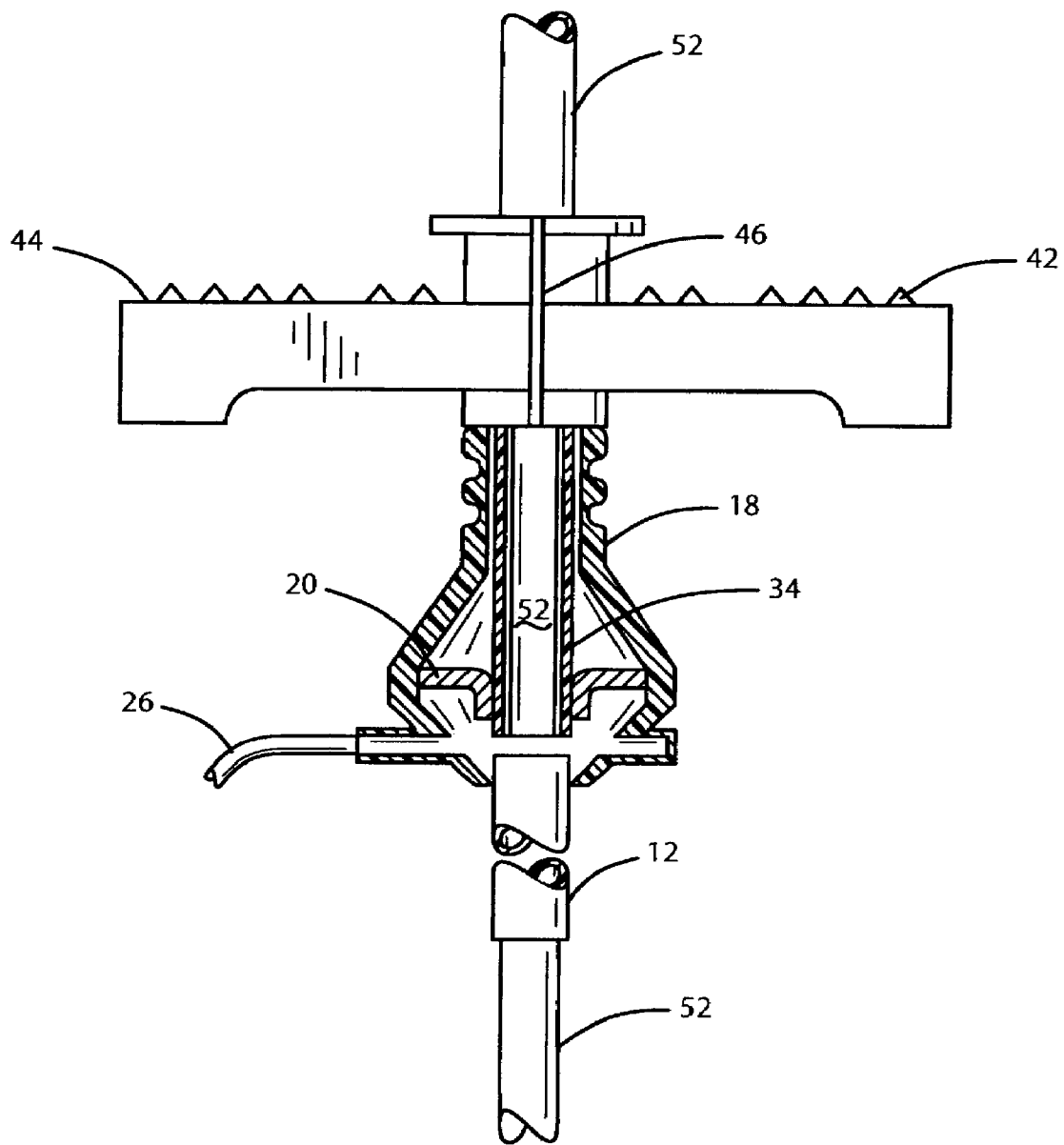
FIG. 4 is a greatly enlarged, cut-away view of the lead insertion tool when used to pass a distal end of a medical lead through a hemostasis valve of an introducer.

In accordance with a first embodiment of the invention, the lead insertion tool consists of a two-piece assembly including a tubular sheath member 30 and a tool dilator 32. The sheath member 30 has a relatively thin-walled, extruded plastic, tubular sheath 34. Affixed to a proximal end 36 thereof is a hub 38 having a Luer fitting 40 on its proximal end. Wings 42 and 44 project laterally from the hub. The hub 38 has longitudinally extending grooves 46 formed inwardly from the outer surface thereof at diametrically located positions. These grooves are not so deep as to intersect with the lumen 48 formed through the hub (FIG. 3). The tubular sheath portion 34 also includes diametrically opposed score lines, as at 50, that are vertically aligned with the grooves 46 and 48.

With the described arrangement, a medical professional is able to split the sheath member 30 into two valves along the grooves 46 and score lines 50 by applying a downward bending force to the wing members 42 and 44.

The lumen 48 of the device is sized to receive the distal end portion of a medical lead 52 through it.

In that the wall thickness of the sheath 34 is only about 0.010 in., it may lack sufficient rigidity to allow it to be passed through the self-closing aperture 22 of the hemostatic valve member 20 of the introducer 10. There is, therefore, provided the tool dilator 32 having a generally rigid shaft 54 which, when inserted through the lumen 48 of the tubular sheath member 30, provides sufficient support to permit the sheath 34 containing the shaft 54 to pass through the self-closing aperture 22. Affixed to the proximal end 56 of the shaft 54 is a Luer lock member 58 for cooperating with the Luer fitting 40 of the sheath member 30. A swivel 60 is rotationally joined to an upper surface of the Luer lock 58.

The swivel 60 includes a central bore that tapers to a lesser diameter of a bore formed longitudinally through the generally rigid shaft 54. The diameter of the bore extending through the shaft 54 is of a size to accommodate a conventional guidewire that can be inserted through the tool dilator 32, the sheath member 30 and the introducer set 10 if desired.

In use, the person involved with implanting the lead 52 may pass a guidewire (not shown) through a hollow trocar used to pierce the selected vein. Leaving the guidewire in place, the needle may then be stripped off from the guidewire and replaced with the introducer set 10 which would be passed over the guidewire and into the puncture wound until the distal end 16 of the introducer set 10 is located within the lumen of the selected vein in which the lead 52 is to be routed in reaching the heart. Once the introducer is in place, its dilator is withdrawn and the combination of the sheath member 30 and the tool dilator 54 that are now locked together by engagement of the Luer lock 58 with the Luer fitting 40 is used to penetrate through the self-closing aperture 22 of the hemostasis valve 20 contained within the hub 18 of the introducer. The wings 42 prevent the sheath member 30 from passing completely through the hemostasis valve and into the blood vessel. Next, the tool dilator 32 is removed from the sheath member 30 and, at this point, a cap (not shown) may be screwed onto the Luer fitting 40 to maintain hemostasis. When the physician is ready to insert the medical lead and advance it into the heart, the cap is removed and the distal end of the lead 52 is inserted through the lumen 48 which is now holding the self-closing aperture open. In that the elastomeric, self-closing hemostasis valve is not acting on the lead, tactile feedback is maintained. Once the lead has been advanced into the heart, the sheath member 30 can be slipped rearward in the proximal direction until the sheath 34 is free of the hub 18 of the introducer. Now, the attending physician may apply finger pressure to the wings 42 and 44 to thereby split the hub 38 along the grooves 46 and 48 and tear the thin-walled sheath 34 along its score line 50. Thus, the sheath member 30 can be completely removed from the lead.

The introducer 10 employed is also designed to be split and pealed free from the lead.

In accordance with an alternate embodiment, the tool dilator 32 can be dispensed with and only the sheath member 30 employed to aid in breaching the self-closing aperture 22 of the hemostatic valve member 20. Here, after the introducer 10 has been placed and its dilator removed, the distal end of the lead 52 may be inserted directly through the bore of the hub 30 and into the lumen of the thin-walled tube 34, but not so far as to project out the distal end of the tubular sheath 34. The combination of the lead 52 filling the lumen of the thin-walled sheath 34 can render the sheath 34 sufficiently rigid to allow it to be passed through the hemostasis valve. Once the assembly has been mated with the hub 18 of the introducer, the lead 52 can be further advanced through the sheath 12 of the introducer and the selected vein into the heart. Again, because the sheath member 30 is splittable, it can readily be removed from the lead once the lead has been positioned.

It should also be mentioned that the length of the tubular sheath 34 is such that when inserted into the hub 18 of the introducer, it will pass through the self-closing aperture 22 but not extend so far as to occlude or block the flow of fluid that may be injected through the side port 24, via the stop cock 28 and the tubing 26.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A lead insertion tool comprising:
   (a) a lead introducer having an elastomeric hemostasis valve with a self-closing aperture;
   (b) a tubular sheath having a relatively thin wall at least one longitudinal groove formed inwardly thereof to facilitate rupture of the sheath along said groove and a lumen sized to receive a medical lead therethrough; and
   (c) a tool dilator having a generally rigid shaft which when inserted through the lumen of the tubular sheath renders the sheath sufficiently rigid to allow insertion of the sheath and dilator through the self-closing aperture of the lead introducer.

2. The lead insertion tool as in claim 1 wherein the elastomeric hemostasis valve is contained in a plastic hub on a proximal end of said lead introducer and said plastic hub includes a side port located distal of the elastomeric hemostasis valve and the tubular sheath is of a length sufficient to pass through the self-closing aperture without blocking said side port.

3. The lead insertion tool as in claim 1 wherein said sheath includes a Luer fitting on a proximal end thereof.

4. The lead insertion tool as in claim 3 wherein the sheath includes a pair of wings extending generally perpendicularly from a longitudinal axis of the sheath to facilitate gripping and rupture of the sheath along said longitudinal groove and to serve as a stop preventing passage of the sheath fully beyond the hemostasis valve.

5. The lead insertion tool as in claim 3 wherein said tool dilator includes a Luer fitting for mating with the Luer fitting on the sheath.

6. The lead insertion tool as in any one of claims 1-5 wherein the shaft of the dilator is sized to substantially occlude the lumen of the tubular sheath.

7. The lead insertion tool as in claim 6 wherein the generally rigid shaft of the tool dilator includes a lumen adapted to receive a guidewire therethrough.

8. A lead insertion tool comprising:
   (a) a lead introducer having an elastomeric hemostasis valve with a self-closing aperture formed therethrough; and
   (b) a tubular sheath having a relatively thin wall with at least one longitudinal groove formed inwardly thereof to facilitate rupture of the sheath along said groove and a lumen sized to receive a lead body therethrough with a predetermined clearance fit, the tubular sheath being sufficiently rigid to be insertable through the self-closing aperture of the hemostasis valve.

9. The lead insertion tool of claim 8 wherein the elastomeric hemostasis valve is contained in a plastic hub on a proximal end of said lead introducer and said plastic hub includes a side port located distal of the elastomeric hemostasis valve and the tubular sheath is of a length sufficient to pass through the self-closing aperture without blocking said side port.

10. A method for facilitating insertion of a relatively limp medical lead through a self-closing aperture in an elastomeric hemostasis valve of a lead introducer comprising the steps of:
   (a) providing a lead introducer having an elastomeric hemostasis valve with a self-closing aperture;
   (b) providing a lead insertion tool having a tubular sheath with a wall defining a lumen, the wall having at least one longitudinal groove formed inwardly thereof to facilitate rupture of the sheath along said groove, said lumen sized to receive a lead body therethrough with a predetermined clearance fit, said tubular sheath being sufficiently rigid when surrounding said lead body to allow insertion through the self-closing aperture of the hemostasis valve;
   (c) inserting a distal end portion of a medical lead into the lumen of the tubular sheath;
   (d) inserting the tubular sheath containing the distal end portion of the medical lead through the self-closing aperture of the elastomeric hemostasis valve;
   (e) sliding the tubular sheath in a proximal direction along the lead body and out from the self-closing aperture leaving the lead body in place; and
   (f) removing the tubular sheath by tearing same along the longitudinal wall.

11. A method for facilitating insertion of a relatively limp medical lead through a self-closing aperture in an elastomeric hemostasis valve of a lead introducer comprising the steps of:
   (a) providing a lead insertion tool having a tubular sheath with a wall defining a lumen, the wall having at least one longitudinal groove formed inwardly thereof to facilitate rupture of the sheath along said groove, said lumen sized to receive a lead body therethrough with a predetermined clearance fit, said tubular sheath being sufficiently rigid when surrounding said lead body to allow insertion through the self-closing aperture of the hemostasis valve;
   (b) providing a tool dilator having a generally rigid shaft of a predetermined length and diameter;
   (c) inserting the tool dilator into the lumen of the tubular sheath;
   (d) passing the tubular sheath with the tool dilator through a self-closing aperture of a hemostasis valve;
   (e) removing the tool dilator from the lead insertion tool; and
   (f) inserting a distal end of the medical lead through the lumen of the lead insertion tool.

12. The method of claim 11 and further including the steps of:
   (a) withdrawing the lead insertion tool from the self-closing aperture; and
   (b) splitting the lead insertion tool along the longitudinal groove to remove the lead insertion tool from surrounding relation with respect to the medical lead.

* * * * *